US00PP37497P2

(12) United States Plant Patent
Mathey

(10) Patent No.: US PP37,497 P2
(45) Date of Patent: Jun. 30, 2026

(54) ***CLETHRA* PLANT NAMED 'SMNCAC'**

(50) Latin Name: *Clethra alnifolia*
Varietal Denomination: SMNCAC

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 19/383,645

(22) Filed: Nov. 8, 2025

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP21,589 P2 * 12/2010 Wood ..... A01H 6/00
Plt./226

* cited by examiner

*Primary Examiner* — Susan McCormick Ewoldt
(74) *Attorney, Agent, or Firm* — C. Anne Whealy

(57) ABSTRACT

A new and distinct cultivar of *Clethra* plant named 'SMNCAC', characterized by its compact, upright to outwardly spreading and uniformly mounding plant habit; vigorous growth habit; freely branching habit; dense and bushy habit; dark green-colored leaves; dense inflorescences with numerous fragrant white-colored flowers; and good container and garden performance.

2 Drawing Sheets

Figure 1:
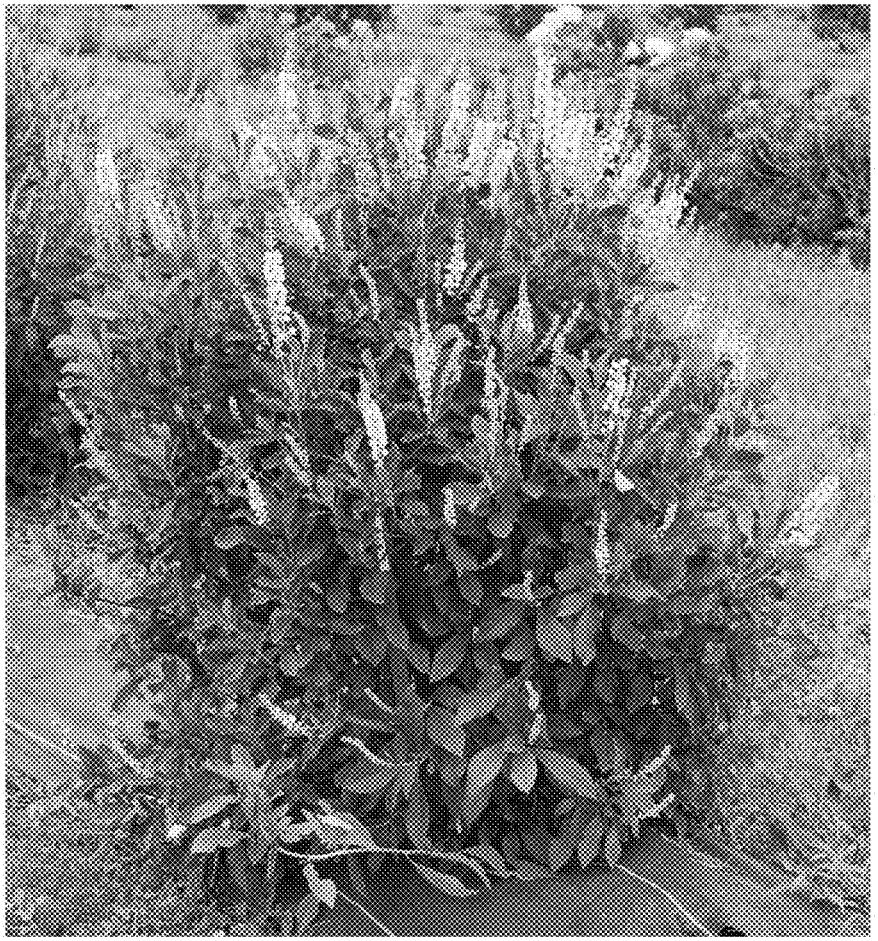

Botanical designation: *Clethra alnifolia.*
Cultivar denomination: 'SMNCAC'.

BACKGROUND OF THE INVENTION

The present invention relates to a new and distinct cultivar of *Clethra* plant, botanically known as *Clethra alnifolia*, commonly known as Sweet Pepperbush or Summersweet and hereinafter referred to by the name 'SMNCAC'.

The new *Clethra* plant is a product of a planned breeding program conducted by the Inventor in Grand Haven, Michigan. The objective of the breeding program is to develop new compact and mounding *Clethra* plants with numerous flowers and good container performance.

The new *Clethra* plant originated from an open-pollination during the summer of 2013 of *Clethra alnifolia* 'Anne Bidwell', not patented, as the female, or seed, parent with an unknown proprietary selection of *Clethra alnifolia*, as the male, or pollen, parent. The new *Clethra* plant was discovered and selected by the Inventor as a single flowering plant within the progeny of the stated open-pollination in a controlled environment in Grand Haven, Michigan during the summer of 2019.

Asexual reproduction of the new *Clethra* plant by softwood cuttings in a controlled greenhouse environment in Grand Haven, Michigan since the summer of 2019 has shown that the unique features of this new *Clethra* plant are stable and reproduced true to type in successive generations of asexual reproduction.

SUMMARY OF THE INVENTION

Plants of the new *Clethra* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNCAC'. These characteristics in combination distinguish 'SMNCAC' as a new and distinct *Clethra* plant:

1. Compact, upright to outwardly spreading and uniformly mounding plant habit.
2. Vigorous growth habit.
3. Freely branching habit; dense and bushy habit.
4. Dark green-colored leaves.
5. Dense inflorescences with numerous fragrant white-colored flowers.
6. Good container and garden performance.

Plants of the new *Clethra* can be compared to plants of the female parent, 'Anne Bidwell'. Plants of the new *Clethra* differ primarily from plants of 'Anne Bidwell' in the following characteristics:

1. Plants of the new *Clethra* are denser and more uniformly mounding than plants of 'Anne Bidwell'.
2. Plants of the new *Clethra* are more floriferous than plants of 'Anne Bidwell'.

Plants of the new *Clethra* can be compared to plants of the *Clethra alnifolia* 'Caleb', disclosed in U.S. Plant Pat. No. 21,589. Plants of the new *Clethra* differ from plants of 'Caleb' in the following characteristics:

1. Plants of the new *Clethra* are denser and more tightly branched than plants of 'Caleb'.
2. Plants of the new *Clethra* have are elliptic in overall plant shape whereas plants of 'Caleb' are globose in overall plant shape.

BRIEF DESCRIPTION OF THE PHOTOGRAPHS

The accompanying colored photographs illustrate the overall appearance of the new *Clethra* plant showing the colors as true as it is reasonably possible to obtain in colored reproductions of this type. Colors in the photographs may differ slightly from the color values cited in the detailed botanical description which accurately describe the colors of the new *Clethra* plant.

The photograph on the first sheet (FIG. 1) is a side perspective view of a typical plant of 'SMNCAC' grown in an outdoor nursery.

Figure 2:
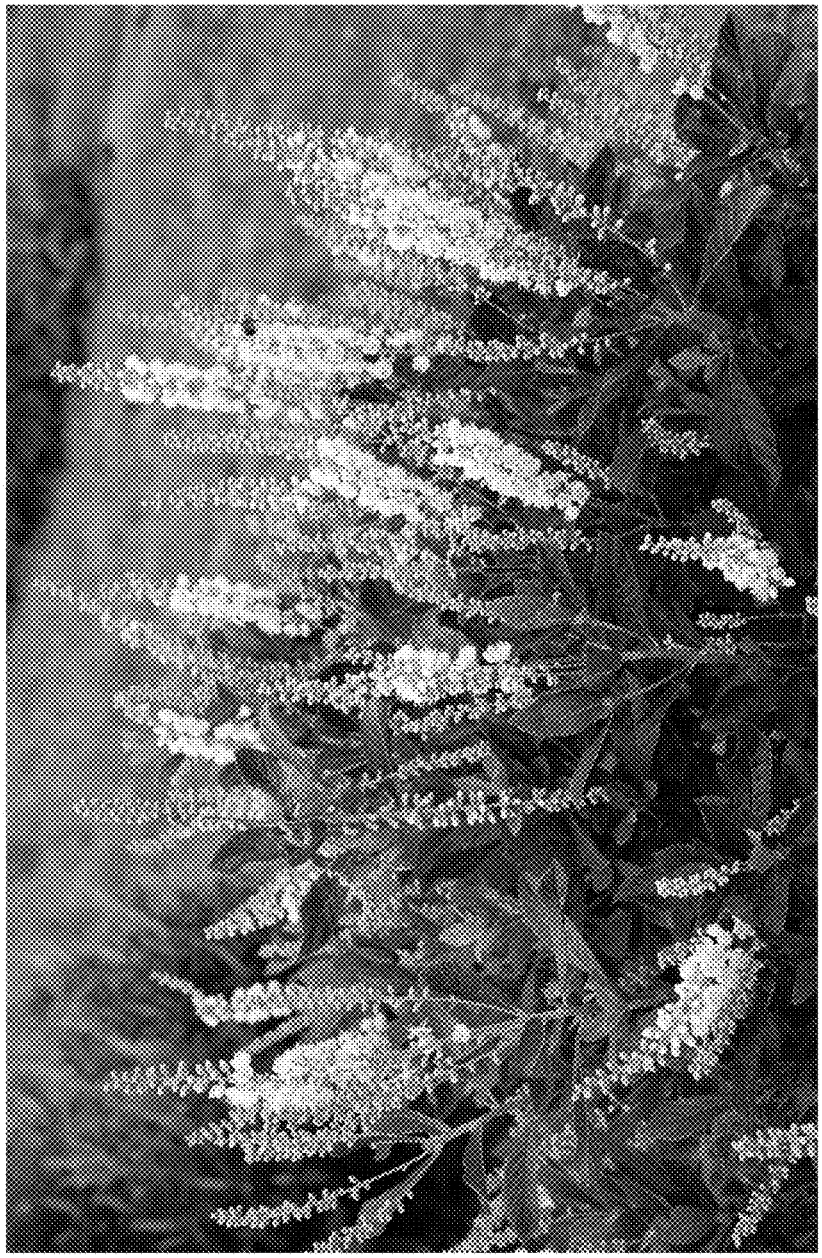

The photograph on the second sheet (FIG. 2) is a close-up view of a typical flowering plant of 'SMNCAC' grown in an outdoor nursery.

Plants used in the photographs were grown during the summer in Grand Haven, Michigan and were three years old.

DETAILED BOTANICAL DESCRIPTION

The following observations and measurements describe plants grown during the summer in three-gallon containers in a polyethylene-covered greenhouse in Grand Haven, Michigan and under cultural practices typical of commercial *Clethra* production. During the production of the plants, day temperatures ranged from 18° C. to 27° C. and night temperatures ranged from ranged from 5° C. to 10° C. Plants were three years old when the detailed description were taken. In the following description, color references are made to The Royal Horticultural Society Colour Chart, 2015 Edition, except where general terms of ordinary dictionary significance are used.

Botanical classification: *Clethra alnifolia* 'SMNCAC'.

Parentage:

*Female, or seed, parent.*—*Clethra alnifolia* 'Anne Bidwell', not patented.

*Male, or pollen, parent.*—Unknown proprietary selection of *Clethra alnifolia*, not patented.

Propagation:

*Type.*—By softwood cuttings.

*Time to initiate roots, summer.*—About 30 days at temperatures about 18° C. to 27° C.

*Time to produce a rooted young plant, summer.*—About four months at temperatures about 18° C. to 27° C.

*Root description.*—Fine to thick; fibrous; typically creamy white to brown in color, actual color of the roots is dependent on substrate composition, water quality, fertilizer, substrate temperature and physiological age of roots.

*Rooting habit.*—Freely branching; dense.

Plant description:

*Plant form and growth habit.*—Perennial shrub; compact, upright to outwardly spreading and uniformly mounding plant habit; overall plant shape, elliptic; vigorous growth habit and moderate growth rate; large and dense inflorescences positioned above the foliar plane.

*Plant height, soil level to top of foliar plane.*—About 75 cm.

*Plant height, soil level to top of floral plane.*—About 85 cm.

*Plant diameter (area of spread).*—About 70 cm.

Lateral branch description:

*Branching habit.*—Freely branching habit with about five to eight primary lateral branches each with about three to six secondary lateral branches developing per plant; tightly branched, dense and bushy habit.

*Length, primary lateral branches.*—About 65 cm.

*Diameter, primary lateral branches.*—About 7 mm.

*Length, secondary lateral branches.*—About 20 cm.

*Diameter, secondary lateral branches.*—About 3 mm.

*Internode length.*—About 2.5 cm.

*Strength.*—Strong.

*Aspect.*—Erect to about 25° from vertical.

*Texture and luster, developing.*—Slightly pubescent; matte.

*Texture and luster, developed.*—Smooth, glabrous; matte.

*Color, developing.*—Close to 145C.

*Color, developed.*—Close to N199C.

Leaf description:

*Arrangement.*—Alternate; simple.

*Length.*—About 6.5 cm.

*Width.*—About 2.5 cm.

*Shape.*—Obovate.

*Apex.*—Acuminate.

*Base.*—Cuneate.

*Margin.*—Serrate.

*Texture and luster, upper surface.*—Smooth, glabrous; somewhat coriaceous; matte.

*Texture, lower surface.*—Mostly glabrous, sparse pubescence along midveins; somewhat coriaceous; matte.

*Venation pattern.*—Pinnate.

*Color.*—Developing leaves, upper and lower surfaces: Close to between 144A and 146B. Fully expanded leaves, upper surface: Close to 147A; venation, close to 145A. Fully expanded leaves, lower surface: Close to 147B; venation, close to 145A.

*Petioles.*—Length: About 7 mm. Diameter: About 1 mm. Texture and luster, upper and lower surfaces: Slightly pubescent; matte. Color, upper and lower surfaces: Close to 145A.

Flower description:

*Flower appearance and arrangement.*—Single rotate flowers arranged in terminal and axillary racemes; freely flowering habit, per plant with about 50 terminal inflorescences and about 100 to 150 axillary inflorescences; 70 to 90 flowers per terminal inflorescence and about 30 to 40 flowers per axillary inflorescence; about 6,000 to 7,000 flowers developing per plant during the flowering season; flowers face upright to slightly outwardly depending on position on inflorescence.

*Natural flowering season.*—Continuous flowering during the summer (July through August) in Michigan.

*Flower longevity.*—Depending on temperature, individual flowers last about two to five days and inflorescences last about two weeks; flowers not persistent.

*Fragrance.*—Moderately to strongly fragrant; fragrance is sweet and spicy, honey and clove-like.

*Terminal inflorescence height.*—About 15 cm.

*Terminal inflorescence diameter.*—About 3 cm.

*Axillary inflorescence height.*—About 10 cm.

*Axillary inflorescence diameter.*—About 2.5 cm.

*Flower size.*—About 1 cm by 1.1 cm.

*Flower depth.*—About 1 cm.

*Flower buds.*—Length: About 5 mm. Diameter: About 3 mm. Shape: Oblong. Texture and luster: Slightly pubescent; matte. Color: Close to 138B.

*Petals*.—Quantity and arrangement: Five in a single whorl. Length: About 8 mm. Width: About 4 mm. Shape: Oblong. Apex: Obtuse. Base: Obtuse. Margin: Entire; not undulate. Texture and luster, upper and lower surfaces: Smooth, glabrous; silky; matte. Color: When opening, upper and lower surfaces: Close to NN155B. Fully opened, upper and lower surfaces: Close to NN155B; color does not change with subsequent development.

*Sepals*.—Quantity and arrangement: Five in a single whorl; fused at the base. Length: About 3 mm. Width: About 2 mm. Shape: Oblong. Apex: Obtuse. Margin: Entire. Texture and luster, upper and lower surfaces: Slightly pubescent; matte. Color: When opening, upper and lower surfaces: Close to 138B. Fully opened, upper and lower surfaces: Close to 138B.

*Peduncles*.—Length: About 15 cm. Diameter: About 2 mm. Strength: Moderately strong. Aspect: Mostly erect. Texture and luster: Slightly pubescent; coarse; matte. Color: Close to 138B.

*Pedicels*.—Length: About 3 mm. Diameter: About 1 mm. Strength: Moderately strong. Aspect: About 45° to 90° from the peduncle axis. Texture and luster: Slightly pubescent; matte. Color: Close to 138B.

*Reproductive organs*.—Androecium: Quantity per flower: About five. Filament length: About 8 mm. Filament color: Close to NN155B. Anther shape: Obcordate. Anther size: About 1 mm by 1 mm. Anther color: Close to 10C. Amount of pollen: Moderate. Pollen color: Close to 10C. Gynoecium: Quantity per flower: About one. Pistil length: About 9 mm. Style length: About 8 mm. Style color: Close to NN155B. Stigma diameter: About 1 mm. Stigma shape: Tri-lobed, oblong. Stigma color: Close to NN155B. Ovary color: Close to 138B.

*Seeds and fruits*.—To date, seed and fruit development has not been observed on plants of the new *Clethra*.

Garden performance: Plants of the new *Clethra* have been observed to have good garden performance and to tolerate rain, wind and to be suitable for USDA Hardiness Zones 4 through 9.

Pathogen & pest resistance: To date, plants of the new *Clethra* have not been observed to be resistant to pathogens and pests common to *Clethra* plants.

It is claimed:

1. A new and distinct *Clethra* plant named 'SMNCAC' as herein illustrated and described.

* * * * *